US00PP29513P3

(12) United States Plant Patent
Uchneat

(10) Patent No.: US PP29,513 P3
(45) Date of Patent: Jul. 17, 2018

(54) ***ZINNIA* PLANT NAMED 'G13163'**

(50) Latin Name: *Zinnia marylandica X Zinnia haageana*
Varietal Denomination: G13163

(71) Applicant: Michael S. Uchneat, Bellefonte, PA (US)

(72) Inventor: Michael S. Uchneat, Bellefonte, PA (US)

(73) Assignee: GardenGenetics LLC, Bellefonte, PA (US)

( * ) Notice: Subject to any disclaimer, the term of this patent is extended or adjusted under 35 U.S.C. 154(b) by 0 days.

(21) Appl. No.: 14/999,535

(22) Filed: May 20, 2016

(65) Prior Publication Data

US 2017/0339814 P1 Nov. 23, 2017

(51) Int. Cl.
*A01H 5/02* (2018.01)

(52) U.S. Cl.
USPC ..... Plt./263.1
CPC ..... *A01H 5/025* (2013.01)

(58) Field of Classification Search
USPC ..... Plt./263.1
CPC ..... A01H 5/025; A01H 5/02; A01H 5/00
See application file for complete search history.

(56) References Cited

PUBLICATIONS

Les Serres Frank Zyromski, Inc.2015-2016 Net Pricing Unrooted Cuttings from HMA Plants (Jul. 1, 2015) retrieved on Jul. 12, 2017, retrieved from the Internet at <http://www.zyromski.com/media/wysiwyg/pdf/SFZ_Bdc_2015-16-_HMA.pdf> pp. 16-17.*
Smug Mug Cultivaris *Zinnia* hybrid ZANY series 2017, retrieved on Jul. 12, 2017, retrieved from the Internet at <https://cultivaris.smugmug.com/CV-EU-Portfolio-Assortment-201/Zinnia-hybrid-ZANY-series/i-BmPDWdx> 2 pp.*

* cited by examiner

*Primary Examiner* — June Hwu
(74) *Attorney, Agent, or Firm* — C. A. Whealy

(57) ABSTRACT

A new and distinct cultivar of *Zinnia* plant named 'G13163', characterized by its upright, outwardly spreading and uniformly mounded plant habit; vigorous growth habit; freely branching habit; dense and full plant form; uniform and freely flowering habit; relatively large single-type inflorescences; rose red-colored ray florets with white-colored apices; florets that are sterile and do not produce seeds; and good resistance to Powdery Mildew.

2 Drawing Sheets

Botanical designation: *Zinnia marylandica* X *Zinnia haageana.*
Cultivar denomination: 'G13163'.

BACKGROUND OF THE INVENTION

The present invention relates to a new and distinct *Zinnia* plant, botanically known as *Zinnia marylandica* X *Zinnia haageana* and hereinafter referred to by the cultivar name 'G13163'.

The new *Zinnia* is the product of a planned breeding program conducted by the Inventor in Bellefonte, Pa. The objective of the breeding program is to create new *Zinnia* plants with attractive flowers and resistance to pathogens.

The new *Zinnia* plant originated from a cross-pollination made by the Inventor on Jul. 29, 2011 in Bellefonte, Pa. of *Zinnia marylandica* 'Zahara Starlight Rose', not patented, as the female, or seed, parent with *Zinnia haageana* 'Persian Carpet', not patented, as the male, or pollen, parent. The new *Zinnia* plant was discovered and selected by the Inventor as a single flowering plant within the progeny of the stated cross-pollination in a controlled greenhouse environment in Bellefonte, Pa. on Jan. 17, 2012.

Asexual reproduction of the new *Zinnia* plant by vegetative terminal cuttings was first conducted in a controlled greenhouse environment in Bellefonte, Pa. on Jan. 17, 2012 and such asexual propagation has shown that the unique features of this new *Zinnia* plant are stable and reproduced true to type in successive generations.

SUMMARY OF THE INVENTION

Plants of the new *Zinnia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'G13163'. These characteristics in combination distinguish 'G13163' as a new and distinct garden-type *Zinnia* plant:

1. Upright, outwardly spreading and uniformly mounded plant habit.
2. Vigorous growth habit.
3. Freely branching habit; dense and full plant form.
4. Uniform and freely flowering habit.
5. Relatively large single-type inflorescences.
6. Rose red-colored ray florets with white-colored apices.
7. Florets that are sterile and do not produce seeds.
8. Good resistance to Powdery Mildew (*Golovinomyces cichoracearum*).

In side-by-side comparisons, plants of the new *Zinnia* differ primarily from plants of the female parent, 'Zahara Starlight Rose' in the following characteristics:

1. Plants of the new *Zinnia* are larger and more vigorous than plants of 'Zahara Starlight Rose'.
2. Ray florets of plants of the new *Zinnia* are mostly rose red in color with white-colored apices whereas ray florets of plants of 'Zahara Starlight Rose' are mostly white in color with rose red-colored bases.
3. Florets of plants of the new *Zinnia* are sterile whereas florets of plants of 'Zahara Starlight Rose' are fertile.

In side-by-side comparisons, plants of the new *Zinnia* differ primarily from plants of the male parent, 'Persian Carpet' in the following characteristics:

1. Plants of the new *Zinnia* are more freely branching than plants of 'Persian Carpet'.
2. Plants of the new *Zinnia* have larger inflorescences than plants of 'Persian Carpet'.
3. Plants of the new *Zinnia* and 'Persian Carpet' differ in ray floret color as florets of plants of 'Persian Carpet' are orange and bronze in color.
4. Florets of plants of the new *Zinnia* are sterile whereas florets of plants of 'Persian Carpet' are fertile.

Plants of the new *Zinnia* can be compared to plants of *Zinnia marylandica* 'Zahara Yellow', not patented. In side-by-side comparisons, plants of the new *Zinnia* differ primarily from plants of 'Zahara Yellow' in the following characteristics:

1. Plants of the new *Zinnia* are larger and more vigorous than plants of 'Zahara Yellow'.
2. Plants of the new *Zinnia* and 'Zahara Yellow' differ in ray floret color as florets of plants of 'Zahara Yellow' are yellow in color.
3. Florets of plants of the new *Zinnia* are sterile whereas florets of plants of 'Zahara Yellow' are fertile.

Plants of the new *Zinnia* can also be compared to plants of *Zinnia marylandica* 'Zahara Coral Rose', not patented. In side-by-side comparisons, plants of the new *Zinnia* differ primarily from plants of 'Zahara Coral Rose' in the following characteristics:

1. Plants of the new *Zinnia* are larger and more vigorous than plants of 'Zahara Coral Rose'.
2. Plants of the new *Zinnia* and 'Zahara Coral Rose' differ in ray floret color as florets of plants of 'Zahara Coral Rose' are dull pink in color.
3. Florets of plants of the new *Zinnia* are sterile whereas florets of plants of 'Zahara Coral Rose' are fertile.

BRIEF DESCRIPTION OF THE PHOTOGRAPHS

The accompanying photographs illustrate the overall appearance of the new *Zinnia* plant showing the colors as true as it is reasonably possible to obtain in colored reproductions of this type. Colors in the photographs may differ slightly from the color values cited in the detailed botanical description which accurately describe the colors of the new *Zinnia* plant.

The photograph on the first sheet comprises a side perspective view of a typical flowering plant of 'G13163' grown in a container, ten weeks from planting rooted cuttings.

The photograph on the second sheet is a close-up view of a typical flowering plant of 'G13163', 14 weeks from planting rooted cuttings.

DETAILED BOTANICAL DESCRIPTION

The aforementioned photographs and following observations and measurements describe plants grown during the spring and summer in 35.5-cm containers in a glass-covered greenhouse in Bellefonte, Pa. and under cultural practices typical of commercial *Zinnia* production. During the production of the plants, day temperatures ranged from 21° to 32° C., night temperatures ranged from 13° C. to 18° C. and light levels ranged from 500 to 1,500 foot candles. Plants were pinched once during propagation and were five months old when the description was taken. In the following description, color references are made to The Royal Horticultural Society Colour Chart, 2007 Edition, except where general terms of ordinary dictionary significance are used.

Botanical classification: *Zinnia marylandica* X *Zinnia haageana* 'G13163'.

Parentage:

*Female, or seed, parent.*—*Zinnia marylandica* 'Zahara Starlight Rose', not patented.

*Male, or pollen, parent.*—*Zinnia haageana* 'Persian Carpet', not patented.

Propagation:

*Type.*—Terminal vegetative cuttings.

*Time to initiate roots, summer.*—About one to two weeks at soil temperatures about 22° C.

*Time to initiate roots, winter.*—About two to three weeks at soil temperatures about 22° C.

*Time to produce a rooted young plant, summer.*—About three to four weeks at ambient temperatures ranging from 22° to 27° C.

*Time to produce a rooted young plant, winter.*—About four weeks at ambient temperatures ranging from 17° to 23° C.

*Root description.*—Medium in thickness, fibrous; close to white in color.

*Rooting habit.*—Freely branching, medium density.

Plant description:

*Plant and growth habit.*—Upright, outwardly spreading and uniformly mounding plant habit; strong and vigorous growth habit.

*Branching habit.*—Freely branching habit, lateral branches developing at potentially every node; dense and full plant form.

*Plant height.*—About 60 cm.

*Plant width.*—About 50 cm.

*Lateral branches.*—Length, longest: About 80 cm. Diameter: About 6 mm to 7 mm. Internode length: About 3 cm to 10 cm. Strength: Strong. Texture: Sparsely pubescent. Color: Close to 146B; younger stems, tinged with close to 34C.

*Leaves.*—Arrangement: Decussate, simple. Length: About 3.5 cm to 8 cm. Width: About 1.5 cm to 3.5 cm. Shape: Narrowly ovate. Apex: Acuminate. Base: Cuneate. Margin: Entire to slightly serrulate. Texture, upper and lower surfaces: Coarse, rough. Venation pattern: Pinnate. Color: Developing and fully expanded leaves, upper surface: Close to 138A; venation, close to 138B. Developing and fully expanded leaves, lower surface: Close to 138B; venation, close to 138B. Petioles: Length: About 1.7 cm to 3 cm. Diameter: About 3 mm to 5 mm. Texture, upper and lower surfaces: Sparsely pubescent. Color, upper and lower surfaces: Close to 146B.

Inflorescence description:

*Type and arrangement.*—Single-type inflorescence form with elliptic-shaped ray florets; disc and ray florets arranged acropetally on a capitulum; inflorescences face mostly upright and held above the foliar plane on strong peduncles.

*Fragrance.*—None detected.

*Flowering response.*—Under natural season conditions, plants flower about six weeks after planting in Pennsylvania.

*Postproduction longevity.*—Inflorescences maintain good color and substance for about three weeks on the plant depending on temperatures; inflorescences persistent.

*Quantity of inflorescences.*—Freely flowering habit with about three inflorescences developing per lateral branch.

*Inflorescence buds.*—Height: About 8 mm. Diameter: About 6 mm. Shape: Oblong to almost spherical. Color: Close to 148A.

*Inflorescence size.*—Diameter: About 5.5 cm to 6 cm. Depth (height): About 1.5 cm. Disc diameter: About 1.8 cm. Receptacle diameter: About 1.8 cm. Receptacle height: About 7.5 mm.

*Ray florets.*—Quantity and arrangement: About 13 to 15 ray florets develop per inflorescence and arranged in a single whorl. Length: About 2.5 cm. Width: About 1 cm. Shape: Elliptic. Apex: Emarginate. Base: Attenuate. Margin: Entire. Orientation: Initially upright, then horizontal. Texture, upper and lower surfaces: Smooth, glabrous; velvety. Color: When opening and fully opened, upper surface: Close to 60B; towards the apex, close to NN155C and 62D; with development, color becomes closer to 60B. When opening and fully opened, lower surface: Close to 145A.

*Disc florets.*—Quantity per inflorescence: About 240. Arrangement: Massed at the center of the receptacle. Length: About 1 cm. Diameter: About 3 mm. Shape: Tubular, elongated. Apex: Five-pointed. Texture, inner and outer surfaces: Smooth, glabrous. Color, immature: Apex: Close to 20A. Mid-section: Close to 157C. Base: Close to 155C. Color, mature: Apex: Close to 17A. Mid-section: Close to 154D. Base: Close to 155C.

*Phyllaries.*—Quantity and arrangement: About 15 to 20 phyllaries develop per inflorescence and arranged in about three to four whorls. Length: About 4 mm to 5 mm. Width: About 4 mm to 5 mm. Shape: Roughly orbicular. Apex: Obtuse. Margin: Entire. Texture, upper and lower surfaces: Smooth, glabrous. Color, upper surface: Close to 152A. Color, lower surface: Close to 148A.

*Peduncles.*—Length, terminal peduncle: About 2 cm. Diameter, terminal peduncle: About 4 mm to 5 mm. Angle: Mostly upright. Strength: Strong. Texture: Sparsely pubescent. Color: Close to 146A.

*Reproductive organs.*—Androecium (present on disc florets only): Stamen number: Five per floret. Filament length: About 1 mm. Filament color: Close to 14B. Anther length: Less than 1 mm. Anther shape: Narrowly oblong. Anther color: Close to 162A. Pollen amount: None observed. Gynoecium (present on ray and disc florets): Pistil length: About 3 mm. Stigma shape: Bi-parted. Stigma color: Close to 16A. Style length: About 4 mm. Style color: Close to 26A. Ovary color: Close to N137D.

*Seeds and fruits.*—Seed and fruit production has not been observed on plants of the new *Zinnia*.

Disease & pest resistance: Good resistance to Powdery Mildew (*Golovinomyces cichoracearum*). Resistance to pests and other pathogens common to *Zinnia* plants has not been observed on plants of the new *Zinnia* grown under commercial production conditions.

Garden performance & temperature tolerance: Plants of the new *Zinnia* have demonstrated excellent garden performance and to tolerate wind, rain, drought and to be suitable for temperatures ranging from 1° to about 38° C.

It is claimed:

1. A new and distinct *Zinnia* plant named 'G13163' as illustrated and described.

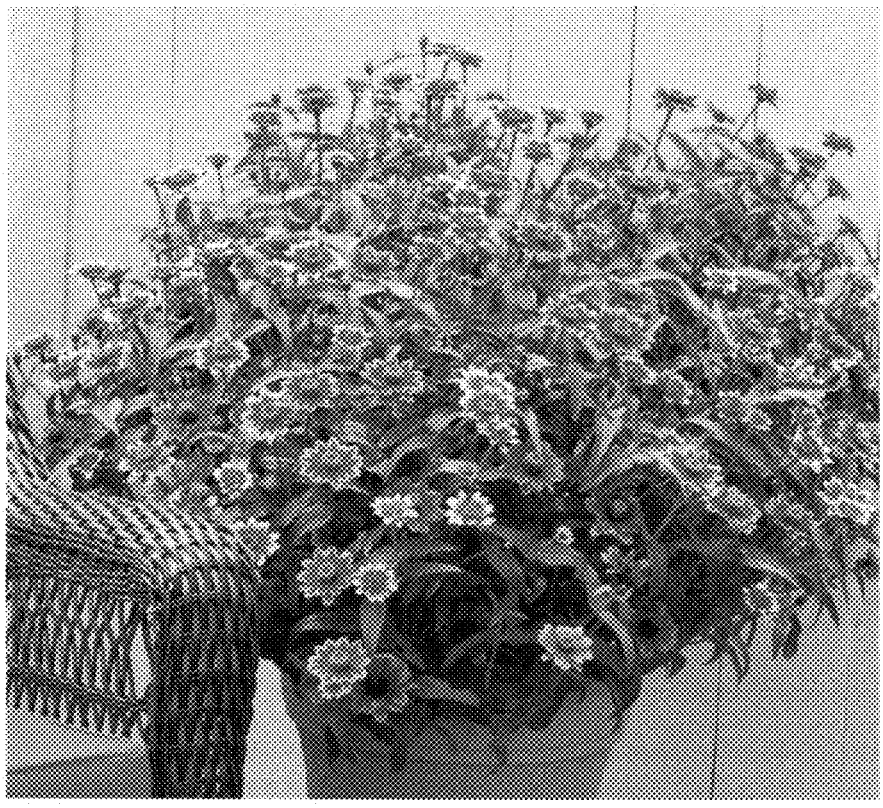

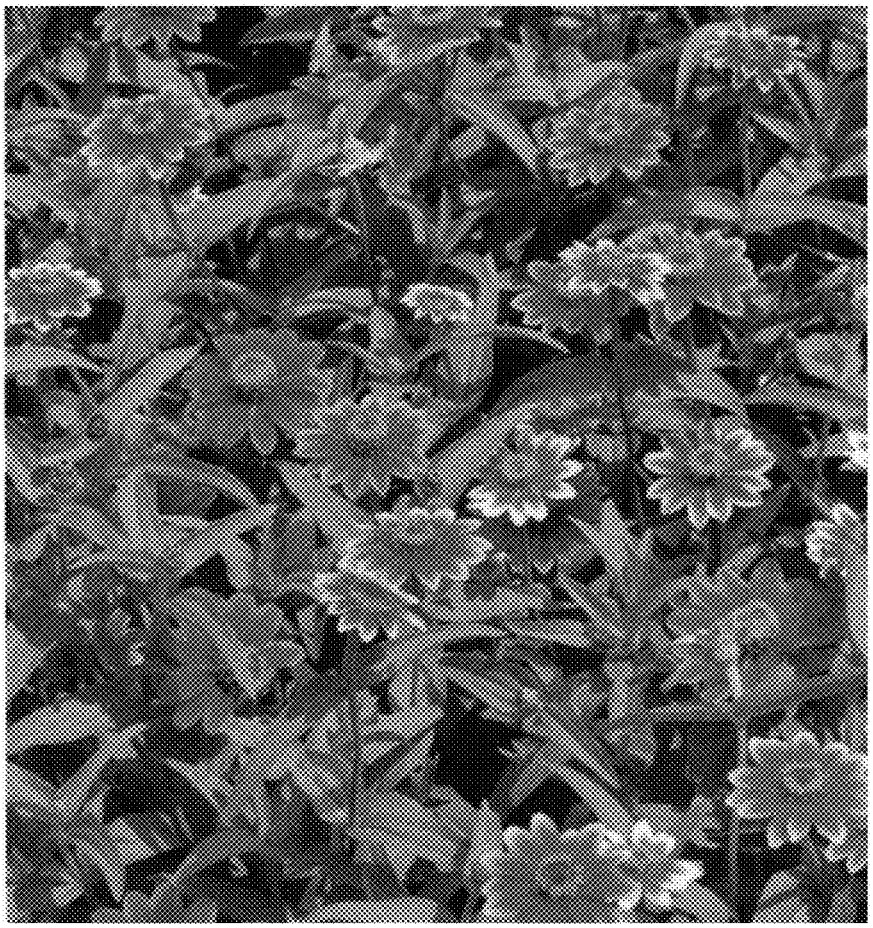

* * * * *